(12) United States Patent
Yoneyama et al.

(10) Patent No.: US 7,499,520 B2
(45) Date of Patent: Mar. 3, 2009

(54) X-RAY IMAGING APPARATUS AND METHOD WITH AN X-RAY INTERFEROMETER

(75) Inventors: Akio Yoneyama, Kawagoe (JP); Yasuharu Hirai, Tosu (JP)

(73) Assignee: Hitachi, Ltd., Tokyo (JP)

( * ) Notice: Subject to any disclaimer, the term of this patent is extended or adjusted under 35 U.S.C. 154(b) by 72 days.

(21) Appl. No.: 11/746,215

(22) Filed: May 9, 2007

(65) Prior Publication Data
US 2008/0019482 A1    Jan. 24, 2008

(30) Foreign Application Priority Data
Jul. 20, 2006    (JP)    ............... 2006-197713

(51) Int. Cl.
*G03H 5/00*    (2006.01)
*G01T 1/36*    (2006.01)
*G21K 1/00*    (2006.01)

(52) U.S. Cl. ............................ 378/36; 378/82; 378/145

(58) Field of Classification Search .................. 378/4, 378/5, 19, 36, 82, 84, 145, 70–73
See application file for complete search history.

(56) References Cited

U.S. PATENT DOCUMENTS

| | | | | |
|---|---|---|---|---|
| 5,173,928 | A * | 12/1992 | Momose et al. | 378/4 |
| 5,930,325 | A * | 7/1999 | Momose | 378/36 |
| 6,195,410 | B1 * | 2/2001 | Cash, Jr. | 378/43 |
| 6,590,954 | B1 * | 7/2003 | Koch | 378/36 |
| 7,113,564 | B2 * | 9/2006 | Yoneyama | 378/36 |
| 7,286,628 | B2 * | 10/2007 | Donnelly et al. | 378/4 |
| 7,346,145 | B2 * | 3/2008 | Yoneyama et al. | 378/82 |

FOREIGN PATENT DOCUMENTS

| | | |
|---|---|---|
| JP | 04-348262 | 12/1992 |
| JP | 09-187455 | 7/1997 |
| JP | 10-248833 | 9/1998 |
| JP | 2005-152500 | 6/2005 |
| JP | 2006-317305 | 11/2006 |
| WO | WO 95/05725 | 2/1995 |

OTHER PUBLICATIONS

U. Bonse, et al., "An X-ray Interferometer", Appl. Phys. Lett., vol. 6, pp. 155, Apr. 15, 1965.
P. Becker, et al., "The Skew-Symetric Two-Crystal X-ray Interferometer" J. Appl. Cryst. vol. 7, pp. 593, Jul. 1974.
R. Fitzgerald, "Phase-Sensitive X-ray Imaging" Physics Today Online, vol. 53, iss. 7, pp. 23, Jul. 2003.

* cited by examiner

*Primary Examiner*—Irakli Kiknadze
(74) *Attorney, Agent, or Firm*—Antonelli, Terry, Stout & Kraus, LLP.

(57) ABSTRACT

A sample which includes a region exhibiting a large density change, such as, bones or lungs and a region exhibiting a small density change, such as, biological soft tissues, and whose measurement is difficult to do for conventional absorption and phase contrast X-ray imaging apparatuses is highly sensitively imaged and observed. In a phase contrast X-ray imaging apparatus using an X-ray interferometer, a reference object whose shape and internal density distribution are analogous to those of a sample and which is known is positioned on an optical path other than an optical path in the interferometer on which the sample is positioned.

20 Claims, 7 Drawing Sheets

FIG.9A     FIG.9B     FIG.9C
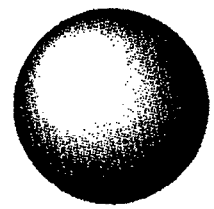
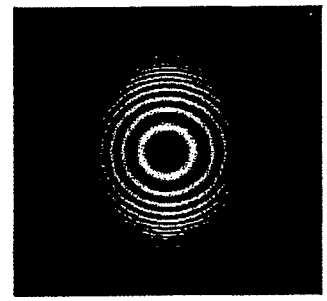
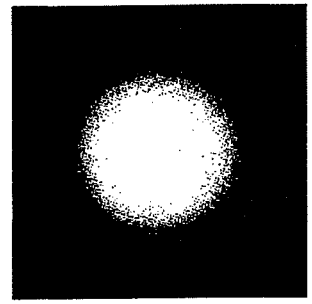
FIG.10
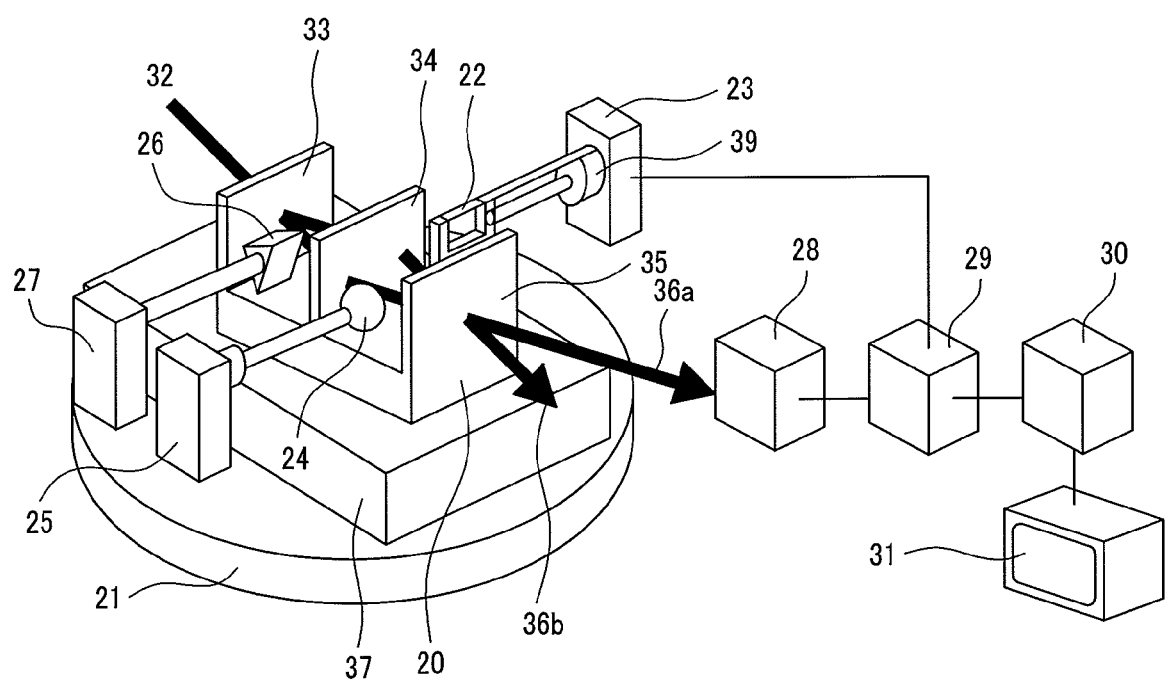

X-RAY IMAGING APPARATUS AND METHOD WITH AN X-RAY INTERFEROMETER

CLAIM OF PRIORITY

The present invention claims priority from Japanese application JP 2006-197713 filed on Jul. 20, 2006, the content of which is hereby incorporated by reference on to this application.

BACKGROUND OF THE INVENTION (1) Field of the Invention

The present invention relates to X-ray imaging apparatuses and methods, or more particularly, to an apparatus and method for non-destructively examining the inside of an entity.

(2) Description of the Related Art

Imaging apparatuses to be used to non-destructively observe the inside of a sample using X-rays include an absorption contract X-ray imaging apparatus that utilizes a change in the intensity of X-rays caused by the sample and a phase contrast X-ray imaging apparatus that utilizes a change in the phase (phase shift) of X-rays.

The former absorption contrast X-ray imaging apparatus is composed mainly of an X-ray source, a sample positioning mechanism, and a detector. X-rays emitted from the X-ray source are irradiated to a sample positioned by the sample positioning mechanism, and X-rays transmitted the sample are detected by the detector. The absorption contrast X-ray imaging apparatus produces an image in which a change in the intensity of X-rays caused by absorption of the sample is shown as an image contrast. Since the principles of measurement and the configuration of the apparatus are relatively simple, the absorption contrast X-ray imaging apparatus is widely used in many fields including a field of medical diagnosis by the name of an X-ray system in which projection data is acquired for two-dimensional observation and by the name of an X-ray CT system in which computed tomography (CT) is performed for three-dimensional observation.

On the other hand, the latter phase contrast X-ray imaging apparatus requires, in addition to the above components, a means for detecting a phase shift. Compared with the absorption contrast X-ray imaging apparatus, the phase contrast X-ray imaging apparatus offers very high sensitivity. Therefore, the phase contrast X-ray imaging enables observations of biological soft tissues without usage of contrast agents and without harmful X-ray exposure. This is because phase shift cross section of a light element is approximately one thousand times larger than absorption cross section Means for detecting a phase shift include, as described in Physics Today (vol. 53, 2000, 23), (1) a method that is disclosed to employ an X-ray interferometer in Japanese Patent Application Laid-Open Nos. 4-348262 and 10-248833, (2) a method that is described to detect an angle of refraction of X-rays using an analyzer crystal in the brochure for the PCT International Publication WO95/05725 and Japanese Patent Application Laid-Open No. 9-187455, and (3) a method utilizing Fresnel diffraction. Among the methods, the method (1) directly detects a phase shift and therefore offers the highest sensitivity. The method (1) having relation to the present invention will be described below.

Japanese Patent Application Laid-Open No. 4-348262 describes a configuration including an X-ray source, a sample positioning mechanism, a detector, and an X-ray interferometer such as a Bonse-Hart interferometer (described in Appl. Phys. Lett. (vol. 6, pp. 155, 1965)) or an interferometer having the Bonse-Hart interferometer divided into multiple crystal blocks (described in J. Appl. Cryst. (vol. 7, pp. 593, 1974)).

FIG. 1 is a perspective view schematically showing the configuration of a Bonse-Hart interferometer. The Bonse-Hart interferometer is formed as one crystal block cut out from a single-crystal ingot monolithically, and that has three wafers equidistantly juxtaposed in parallel with one another (serving as a beam splitter 1, a mirror 2, and an analyzer 3). Incident X-rays 4 are split into two beams of a beam 5 and a beam 6 by the first wafer (beam splitter 1), reflected from the second wafer (mirror 2), and recombined by the third wafer (analyzer 3). Consequently, two interference beams 7 and 8 are formed. If a sample 9 is positioned in the path of the beam 5 or 6, a change in the phase of the beam caused by the sample changes in the intensities of the interference beams 7 and 8 due to superposition (interference) of the waves. By taking advantage of the principle, an image showing a change in a phase (a phase contrast image) can be obtained by the changes in the intensities of the interference beams 7 and 8 are detected by an image detector or the like.

Imaging apparatuses in which the phase contrast imaging method and an ordinary X-ray CT technique are combined in order to enable three-dimensional non-destructive observation, include an imaging apparatus described in Japanese Patent Application Laid-Open No. 4-348262. Similarly to ordinary X-ray CT, X-rays are irradiated to a sample in multiple directions, and a phase contrast tomographic image of the sample is reproduced by computing using respective projection data sets.

Light elements, such as oxygen or carbon, are nearly transparent to X-rays, and almost incident X-rays are not absorbed by the light element. Therefore, a change in an intensity derived from absorption by a subject is very small, and observation with high sensitivity of biological soft tissues or organic materials are difficult by using absorption contrast X-ray imaging method. In efforts to compensate insufficient sensitivity, a contrast agents is used or an exposure time is extended. However, this induces a problem in that a region capable of being imaged is limited or an exposure increases.

On the other hand, the sensitivity of phase contrast X-ray image is sufficiently high, but complex computation called phase unwrapping is needed to obtain phase contrast images. As shown in FIG. 2, a change $\alpha$ in a phase caused by a sample is detected as a value $\alpha'$ rounded off (wrapped) to fall within 0 to $2\pi$ ($\alpha'=\alpha-\text{Int}(\alpha/2\pi)\times 2\pi$). Therefore, it is required a process for restoring the true change a in a phase (phase unwrapping) using a calculation method described in, for example, Japanese Patent Application Laid-Open No. 2001-153797. Furthermore, X-rays are refracted in a region of a sample in which the density is spatially abruptly varied caused by the complex shape or the internal structure of the sample. The X-rays are deviated from their original optical path, and superposed on a beam other than a reference beam as described later with reference to FIG. 4B and FIG. 4C. Since the coherence length of X-rays is so short as to range from several micrometers to several tens of micrometers, this deviation induces a decrease in sharpness (visibility) of an interference pattern or disappearance of interference fringes. And the unwrapping cannot be performed normally, and the change $\alpha$ cannot be accurately restored.

In efforts to avoid the foregoing problem, an example like the one described in Japanese Patent Application Laid-Open No. 7-209212 may be immersed in a liquid in order to decrease the difference in density between the sample and its surroundings. In this case, the influence of a shape can be minimized but an rapid change in density inside the sample cannot be coped with. Moreover, an object to be measured is limited to a specific one.

FIG. 3 is an explanatory diagram of observable regions of the conventional absorption, phase contrast X-ray imaging methods, and the present invention. According to the conventional absorption and phase contrast X-ray imaging methods, a region of a density change in a sample to which each of the X-ray imaging methods is sensitive is limited to an extreme region of large or small values. This indicates that the X-ray imaging methods cannot enable observation at a high density resolution of a sample in which a region exhibiting a large density change, for example, bones and lungs, and a region exhibiting a small density change, such as, biological soft tissues are mixed.

SUMMARY OF THE INVENTION

An object of the present invention is to provide an imaging apparatus and method that increases, as shown in FIG. 3, a density-change dynamic range offered by the phase contrast X-ray imaging method so that the range of a density change to which the phase contrast X-ray imaging method is sensitive will cover the range of values of a density change to which the absorption contrast X-ray imaging method is sensitive, and that enables observation of a sample, in which a region exhibiting a large density change and a region exhibiting a small density change are mixed, at the same density resolution as the phase contrast X-ray imaging method does.

A means for accomplishing the object of the present invention will be described in conjunction with a typical X-ray interferometer shown in FIG. 4. FIG. 4A to FIG. 4C illustratively show the states of beams in the X-ray interferometer. As shown in FIG. 4A, in the X-ray interferometer 10, an incident X-ray beam 14 is split into a first beam 15 and a second beam 16 by a splitter 11. The beams have the optical paths thereof changed by a mirror 12, and are recombined by an analyzer 13. Consequently, interference beams 17a and 17b are formed.

Assuming that $I_1$ and $I_2$ denote the intensities of the first and second beams 15 and 16, the intensity I of the interference beam 17 is given by the following equation (1):

$$I = I_1 + I_2 + 2r\sqrt{I_1 \cdot I_2} \cos \phi \tag{1}$$

where r denotes a degree of coherence, and $\phi$ denotes a phase difference between the first and second beams 15 and 16. The degree of coherence r is given by the equations (2) and (3) as a function of the wavelength $\lambda$ of the incident X-ray beam 14, a divergence angle W, and a gap $\Delta x$ on the analyzer 13 between the paths of the first and second beams 15 and 16.

$$r = 2\frac{J(v)}{v} \tag{2}$$

$$v = \frac{2\pi W \Delta x}{\lambda} \tag{3}$$

where J denotes the Bessel function of the first kind.

Assuming that no obstacle is present on the paths of the first and second beams 15 and 16 and the shape of the X-ray interferometer 10 is ideal, the paths of the first and second beams 15 and 16 on the analyzer 13 perfectly coincide with each other. This means that the gap $\Delta x$ equals 0 and the degree of coherence r equals 1 (visibility is 100%). On the other hand, if the interferometer has an error in terms of shape, that is, suffers deformation, the paths of the first and second beams 15 and 16 are deviated. This means that the gap $\Delta x$ is not 0. The degree of coherence r decreases along with an increase in the gap $\Delta x$. When the value v is almost 3.8317, the degree of coherence r equals 0, that is, the first and second beams do not interfere with each other. For easy calculation, the shape of the X-ray interferometer 10 shall be regarded as being ideal.

Assuming that a sample 18 positioned on the path of the first beam 15 in the X-ray interferometer 10 causing a change $\Delta I$ in an intensity, a change $\Delta p$ in a phase, a change $\Delta \theta$ in a propagating direction of X-rays is, as shown in FIG. 4B, X-rays transmitted the sample 18 are refracted as indicated with a dot line 17b'. The equation (1) is modified into the following equation (4):

$$I' = (I_1 - \Delta I) + I_2 + 2r'\sqrt{(I_1 - \Delta I) \cdot I_2} \cos(\phi + \Delta p) \tag{4}$$

where r' denotes a degree of coherence changed along with the change $\Delta \theta$ in a propagating direction of X-rays.

Assuming that R denotes the distance between the center position of the sample 18 and the center position of the analyzer 13, the positional gap $\Delta x'$ on the analyzer between the first and second beams 15 and 16 which is derived from the change $\Delta \theta$ in a propagating direction of X-rays is given by the following equation (5):

$$\Delta x' = R \Delta \theta \tag{5}$$

Consequently, using the equations (2) and (3), the changed degree of coherence r' is expressed as a function of the change $\Delta \theta$ in a propagating direction of X-rays by the following equation (6):

$$r' = \frac{2J(kWR\Delta\theta)}{kWR\Delta\theta} \tag{6}$$

where $k = 2\pi/\lambda$ is established.

Assuming that a reference object 19 are positioned on the path of the second beam 16, and having known shape and internal density which is causing a change $\Delta I'$ in an intensity, a change $\Delta p'$ in a phase, and a change $\Delta \theta'$ in a propagating direction of X-rays is, as shown in FIG. 4C, X-rays transmitted the reference object 19 are refracted as indicated with a dot line 17a'. And the equation (4) is further modified into the equation (7) presented below.

$$I'' = (I_1 - \Delta I) + (I_2 - \Delta I') + 2r'' \sqrt{(I_1 - \Delta I) \cdot (I_2 - \Delta I')} \cos(\phi + \Delta p + \Delta p') \tag{7}$$

where r'' denotes a degree of coherence changed along with the change $\Delta \theta'$ in a propagating direction of X-rays.

Assuming that R' denotes the distance between the reference object 19 and analyzer 13, the positional gap $\Delta x''$ on the analyzer between the first and second beams 15 and 16 is given by the equation (8) similar to the equation (5).

$$\Delta x'' = R' \Delta \theta' \tag{8}$$

Using the equations (2), (3), and (6), the changed degree of coherence r'' is expressed as follows:

$$r'' = \frac{2J(kW(R\Delta\theta - R'\Delta\theta'))}{kW(R\Delta\theta - R'\Delta\theta')} \tag{9}$$

Consequently, assuming that a reference object which causes the change $\Delta \theta'$ in a propagating direction of X-rays that is almost equal to the change Δθ therein caused by the sample and whose shape and three-dimensional density distribution are analogous to those of the sample is positioned at which the distance R between the sample and analyzer is almost equal to the distance R' between the reference object and analyzer, the product of RΔθ is almost equal to the product of R'Δθ' is satisfied, and therefore the difference Δx'−Δx" between the positional gaps comes to nearly zero (r" is nearly 1). At the same time, since the change Δθ in a propagating direction of X-rays is proportional to the spatial derivative of the change Δp in a phase, the sum Δp+Δp' of the changes in a phase gets smaller accordingly. Consequently, the conventional issues of the degradation in visibility and an unwrapping error can be solved.

Consequently, even a sample in which a region exhibiting a large density change, such as, bones or lungs and a region exhibiting a small density change, such as, biological soft tissues are mixed can be observed at a high density resolution.

According to the present invention, a reference object whose shape and internal density are analogous to those of a sample is positioned on the path of a reference wave in an X-ray interferometer. Thus, a rapid phase shift can be suppressed. Moreover, even a sample of a biological soft tissue which includes a region exhibiting a large density change, such as, bones or lungs, and whose measurement has been difficult to do for a conventional phase contrast X-ray imaging apparatus can be observed with high sensitivity.

BRIEF DESCRIPTION OF THE DRAWINGS

The invention will be more particularly described with reference to the accompanying drawings, in which:

FIG. 9A to FIG. 9C show the shape of a virtual sample substituted for an actual sample for use in measurement employed in the first embodiment, and the results of measurement (sample image) obtained by performing numerical calculation;

FIG. 10 shows the configuration of an X-ray imaging apparatus in accordance with the second embodiment of the present invention;

DESCRIPTION OF THE PREFERRED EMBODIMENTS

Figure 1:
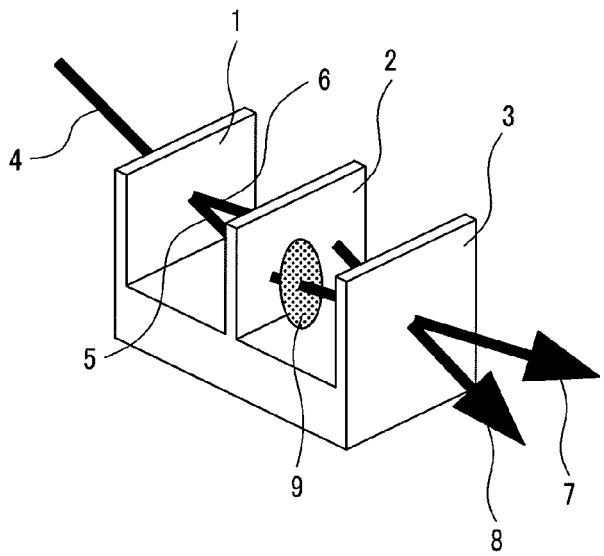
FIG. 1 is a perspective view schematically showing the structure of a Bonse-Hart interferometer.
Figure 2:
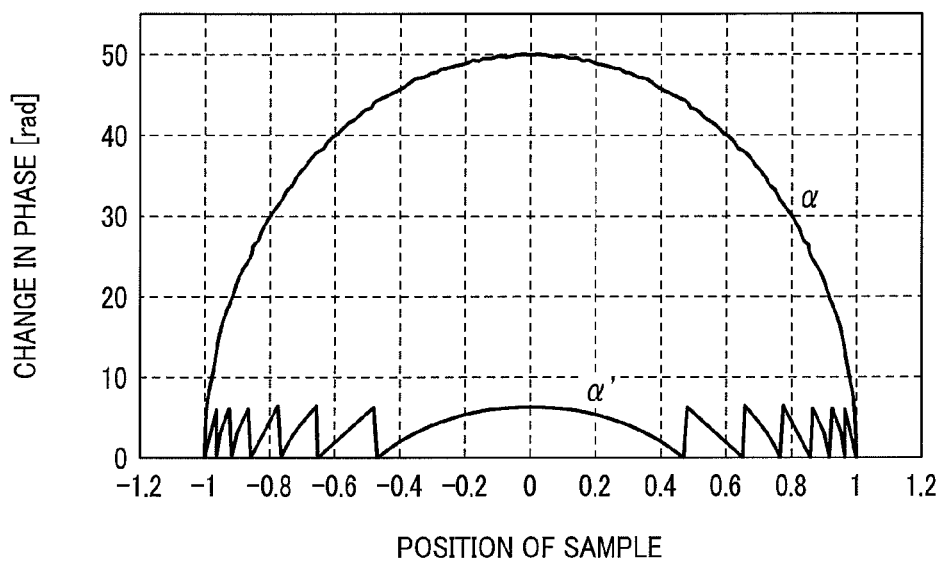
FIG. 2 is an explanatory diagram graphically showing a change α in a phase caused by a sample that is detected as a value α' rounded off (wrapped) to fall within a range from 0 to 2π (α'=α−Int(α/2π)×2π) during measurement performed as part of phase contrast X-ray imaging.
Figure 3:
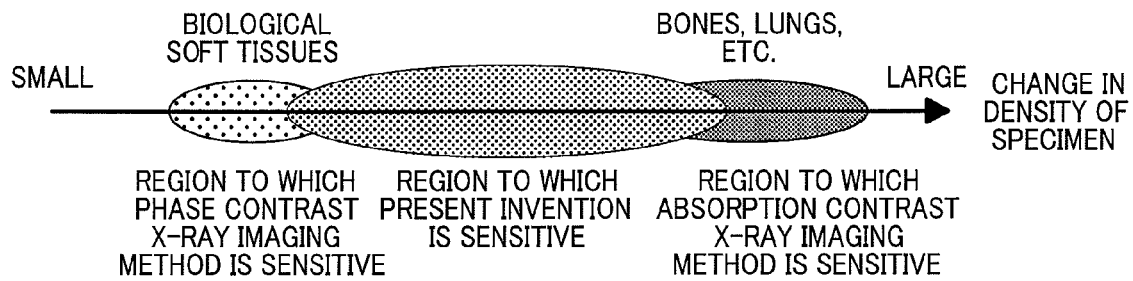
FIG. 3 is an explanatory diagram showing restrictions imposed on regions made observable by a conventional absorption and phase contrast X-ray imaging methods respectively and a region made observable by the present invention.
Figure 4A:
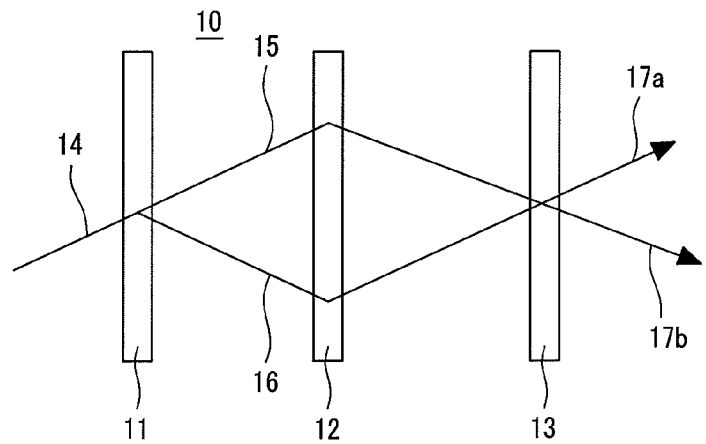
FIG. 4A to FIG. 4C illustratively show the states of beams in an X-ray interferometer.
Figure 4B:
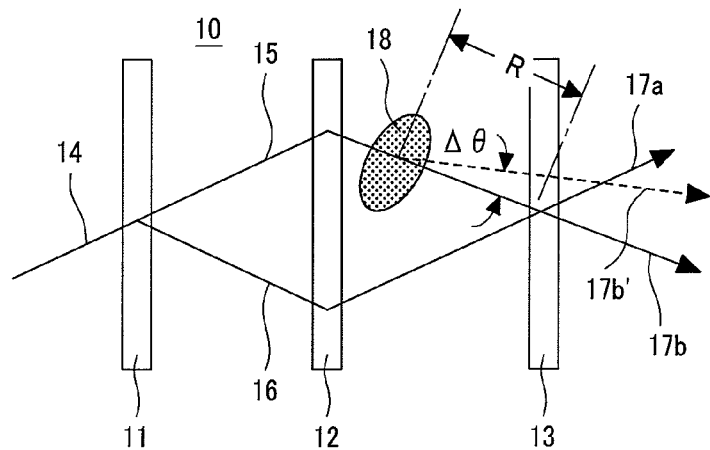
Figure 4C:
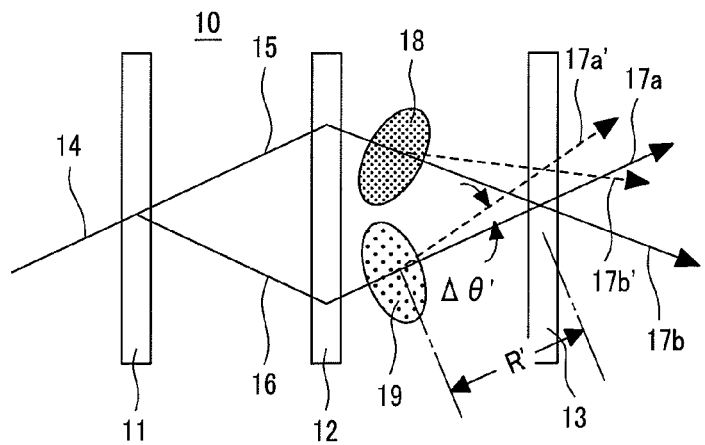

Referring to the drawings, embodiments of the present invention will be described below. In the drawings to be referred to later, the same reference numerals are assigned to components having the same capabilities. An iterative description will be omitted.

First Embodiment

Figure 5:
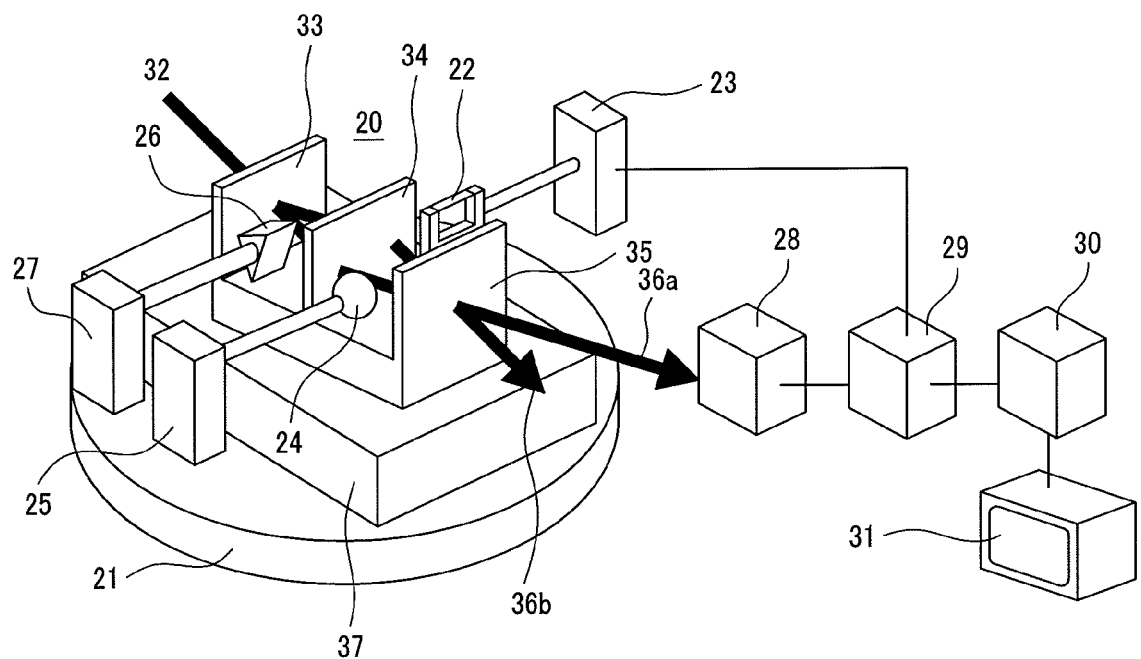
FIG. 5 shows the configuration of an X-ray imaging apparatus in accordance with the first embodiment of the present invention.

FIG. 5 shows the configuration of an X-ray imaging apparatus in accordance with the first embodiment of the present invention. The imaging apparatus of the first embodiment includes: an X-ray interferometer 20 including a splitter 33, a mirror 34, and an analyzer 35; an X-ray interferometer aligning mechanism 21, a sample holder 22, a sample holder positioning mechanism 23, a reference object 24, a reference object positioning mechanism 25, a wedge 26, a wedge positioning mechanism 27, an X-ray image detector 28, a control unit 29, a processing unit 30, and a display unit 31.

Herein, a Bonse-Hart interferometer shown in FIG. 1 is adopted as the X-ray interferometer 20. In the interferometer, X-rays 32 incident on the X-ray interferometer 20 are split, reflected, and then recombined sequentially by a splitter 33, a mirror 34, and an analyzer 35 respectively. Consequently, a first interference beam 36a and a second interference beam 36b are formed. The first and second interference beams 36a and 36b are detected by the X-ray image detector 28. The processing unit 30 calculates a phase shift caused by a sample, and a produced sample image is displayed on the display unit 31. At this time, the sample is positioned on the path of one of beams, into which the X-rays are split, in the interferometer by means of the sample holder 22 positioned by the sample holder positioning mechanism 23. Moreover, the reference object 24 is positioned on the path of the other beam by the reference object positioning mechanism 25.

An X-ray interferometer having the splitter 33, mirror 34, and analyzer 35 thereof shaped and spaced with the precision of several micrometers or less should be adopted as the X-ray interferometer 20. Since the coherence length of X-rays is generally on the order of several micrometers to several tens of micrometers, such an X-ray interferometer enables to form an X-ray interference pattern of good visibility (a image formed by the first and second interference beams 36a and 36b). And actually measured signal intensity increases, measurement can be performed with highly precisely. When the thicknesses of the splitter 33, mirror 34, and analyzer 35 respectively are smaller, the spread of an X-ray beam in wafers is suppressed, and higher spatial resolution can be attained. However, according to consideration of mechanical strength, when the wafers are small parallelepipeds of about 5 mm in size, the thicknesses should be about several tens of micrometers or more. When the wafers are large parallelepipeds of about 20 mm in size, the thicknesses should range from 100 micrometers to about 1 mm. Moreover, a single crystal that hardly makes a transition, for example, a FZ silicon single-crystal ingot should be adopted as the base material of the X-ray interferometer 20. The crystal dislocation causes an X-ray beam to markedly deform. Therefore, the smaller the number of times of dislocation is, the better the quality of a formed X-ray interference pattern is.

A rotational mechanism having the precision of 1/200 arcsec. or more should be adopted as the X-ray interferometer aligning mechanism 21. The visibility of an X-ray interference pattern varies quite sensitively to the angle of incidence of X-rays. For example, even when the angle of incidence changes by only 1/100 arcsec., the visibility is degraded from 60% to 20%. Consequently, the employment of the mechanism offering the precision makes it possible to align the X-ray interferometer with the direction of the angle of incidence that enables formation of a highly visible X-ray interference pattern.

Moreover, the X-ray interferometer 20 is very sensitive to mechanical stress. Even when very small extraneous force acts on the X-ray interferometer, an X-ray interference patter is distorted. Therefore, the X-ray interferometer 20 should be placed on a flat base 37 positioned on the X-ray interferometer aligning mechanism 21. Moreover, the crystal wafers serving as the splitter 33, mirror 34, and analyzer 35 respectively are deformed with airflow around the X-ray interferometer or sound pressure derived from noises. Consequently, the X-ray interference pattern may be distorted. Therefore, the X-ray interferometer 20 and X-ray interferometer aligning mechanism 21 may be entirely hooded. In this case, the X-ray interferometer would be unsusceptible to the surroundings, and an excellent X-ray interference pattern could be formed.

When the reference object 24 has a shape and an internal density that are as analogous as possible to those of a sample, the positional gap on the analyzer 35 of a beam transmitted the sample and a beam transmitted the reference object 24, that is, degradation in visibility can be minimized. When the sample is a living body, a phantom simulating the region of the sample should be adopted as the reference object 24. For example, when the head of a small animal is measured, the reference object 24 is produced by firming the skull of an individual, which belongs to the same species as the small animal, using an organic material or the like so that the appearance thereof will resemble that of the small animal. In this case, for example, when the sample is a mouse, since the appearance of the mouse changes along with growth, reference objects resembling the sizes of mice whose ages range from one month to twelve months should be prepared. Moreover, when the sample is a biological tissues with disease, if a normal tissues is adopted as the reference object 24, only a change derived from a disease can be sampled.

Figure 6:
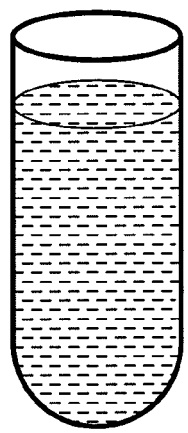
FIG. 6 shows an example in which a sample to be measured is put in a test tube together with a solvent.

FIG. 6 shows an example in which a sample to be measured is put into a test tube together with a solvent. When a sample is put into a test tube together with a solvent, the same solvent is put into the same kind of test tube and used as the reference object 24. Thus, a change occurring in the test tube can be directly detected.

An X-Z positional stage driven by a stepping motor can be adopted as the sample holder positioning mechanism 23 and reference object positioning mechanism 25 alike. Anyhow, the sample holder positioning mechanism 23 and reference object positioning mechanism 25 should be able to remotely position a sample and the reference object 24 respectively. Thus, the sample and reference object 24 can be accurately positioned with respect to respective beams. Eventually, a highly visible X-ray interference pattern can be formed.

A pickup tube Saticon or a combination of a scintillator, an optical focusing system (lenses or an optical fiber), and a CCD camera can be adopted as the X-ray image detector 28. Owing to the high X-ray detecting efficiency, highly precise measurement can be achieved for a shorter measurement time.

Next, a method of producing an image in which a phase difference caused by a sample is shown as a contrast will be described in relation to the first embodiment.

Referring to FIG. 5, the intensities of the interference beams 36a and 36b vary depending on the difference between the phases of the beams which is caused by the sample and reference object 24. Consequently, the phase difference caused by the sample can be obtained according to a sub-fringe measuring method that is based on the Fourier transform method or the like and described below. When the wedge 26 made of acrylic or any other material that little absorbs X-rays is positioned on one of the paths of beams using the wedge positioning mechanism 27, interference moiré fringes are superposed on an interference pattern in a direction (X) orthogonal to the tilting direction of the wedge. The intensity distribution in the interference pattern is expressed by the equation (10) presented below.

$$I(x,y)=\alpha(x,y)+c(x,y)\exp(2\pi i f_o x)+c^*(x,y)\exp(-2\pi i f_o x) \quad (10)$$

Herein, $$c(x, y) = \frac{1}{2}A(x, y)\exp(i\Delta p(x, y)) \quad (11)$$

where $\alpha$ denotes a background intensity distribution having no relation to the interference fringes, A denotes the amplitude of the interference fringes, $\Delta p$ denotes the phase difference between beams transmitted a sample and a reference object respectively, and $f_o$ denotes a spatial frequency in an x direction of moiré fringes. Moreover, * denotes a complex conjugate.

When the intensity distribution expressed by the equation (10) is Fourier-transformed into a function of a variable x, a spatial frequency spectrum $I_F(f,y)$ in the x direction is expressed by the equation (12) presented below. Herein, $\alpha_F$, $c_F$, and $c_F^*$ denote quantities Fourier-transformed from quantities of $\alpha$, c, and c* in the equation (10).

$$I_F(f,y)=\alpha_F(f,y)+c_F(f-f_o,y)+c_F^*(f+f_o,y) \quad (12)$$

Assuming that the angle of the wedge 26 is determined so that the space between adjoining ones of moiré fringes will be sufficiently narrow for the structure of a sample, the values of the $\alpha_F$, $c_F$, and $c_F^*$ quantities in the equation (12) represent nearly perfectly separated spectra. At this time, the values of the $c_F$ or $c_F^*$ quantity alone are sampled, and the $f_o$ values are zeroed. The resultant function is then inversely Fourier-transformed in order to obtain the quantity c containing information on a change in a phase. The phase difference $\Delta p$ can be obtained by calculation of an argument.

Consequently, the shape of the reference object 24 and the internal density distribution thereof are known, the phase difference $\Delta p''$ in used X-ray energy caused by the reference object can be calculated. By simply subtracting the $\Delta p''$ value from the $\Delta p$ value, the phase difference $\Delta p'$ caused by the sample can be obtained. The foregoing processing is performed by the processing unit 30. An image in which the phase difference Δp' caused by the sample is shown as a contrast is displayed on the display unit 31.

Figure 7:
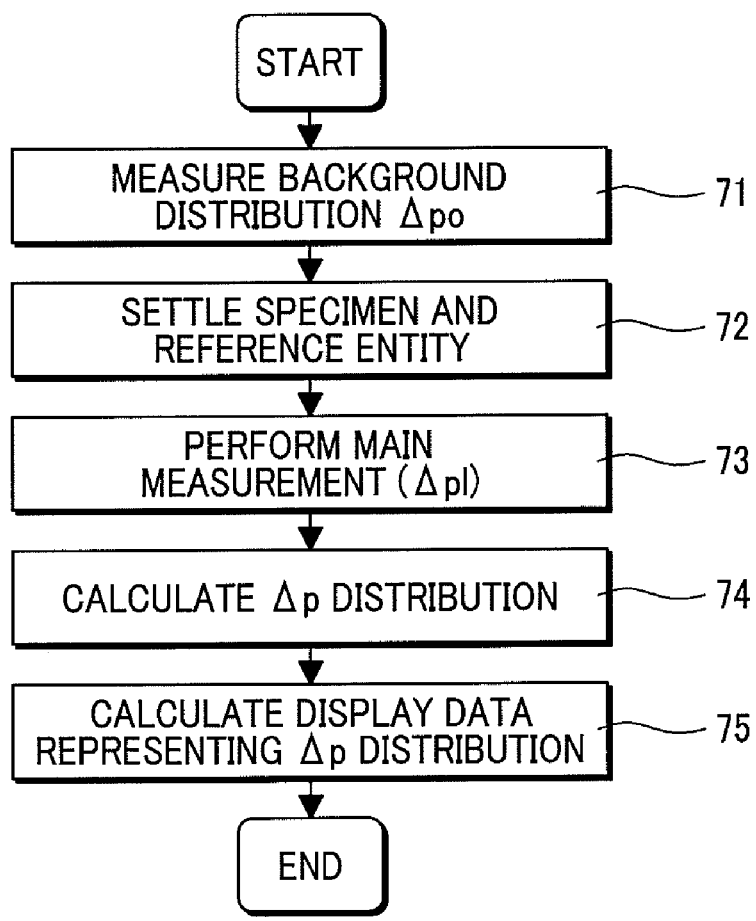
FIG. 7 is a flowchart describing a procedure of eliminating a background distribution from a signal, which represents a phase difference Ap, during measurement employed in the first embodiment.

FIG. 7 is a flowchart describing a procedure for eliminating a background distribution from a signal representing the phase difference Δp during measurement employed in the first embodiment. If crystalline distortion or the like remains in the X-ray interferometer 20, a background distribution of phase shifts (spatial distribution of phase shifts attained when a sample is absent) becomes uneven. Eventually, a sample image cannot be accurately viewed. In the first embodiment, the background distribution is eliminated from the signal Δp according to the procedure described in FIG. 7.

At step 71 (measurement of a background), before a sample and a reference object are positioned, a background distribution (Δpo) of phase shifts is calculated using the Fourier transform method.

At step 72, the sample holder 22 and sample holder positioning mechanism 23 are used to place the sample on an associated optical path, and the reference object positioning mechanism 25 is used to place the reference object 24 on an associated optical path. The positions of the sample and reference object 24 are adjusted so that the positions will be nearly identical on the respective beams.

At step 73 (main measurement), a distribution (Δp1) of phase values that is a combination of the background distribution and a distribution of phase shifts affected by the sample and reference object is obtained.

At step 74, a distribution Δp (=Δp1−Δp0) of phase change values caused by the sample and reference object is calculated from the phase distributions obtained at steps 71 and 73 respectively.

At step 75, the phase distribution obtained at step 74 is used to calculate display data representing the distribution.

However, a spatial frequency of this method is generally determined by the space between adjoining ones of carrier fringes in an X-ray interference pattern formed by the wedge 26, and is therefore on the order of several hundreds of micrometers. Some samples cannot therefore be observed with sufficiently high spatial resolution because of the insufficient spatial frequency. This issue can be solved by adopting a sub-fringe measurement called a fringe scanning method described below. According to the fringe scanning method, the wedge 26 is moved orthogonally to X-rays using the wedge positioning mechanism 27 in order to change the phase of X-rays, and multiple interference patterns derived from different phase difference values are then formed. The formed interference patterns are used to calculate a phase shift. When M interference patterns are derived from phase shift values that vary in units of an equal value, a change in a phase Δp can be calculated according to the equation (13) presented below.

$$\Delta p = \text{Arg}\left[\sum_{k=0}^{M-1} I_k \exp\left(-2\pi i \frac{k}{M}\right)\right] \quad (13)$$

where Arg denotes calculation of an argument.

Similarly to the measurement based on the Fourier transform method, the shape of the reference object 24 and the internal density distribution thereof are known, a phase difference Δp'' in used X-ray energy caused by the reference object can be calculated, and a phase difference Δp' caused by the sample can be obtained by simply subtracting the Δp'' value from a Δp value.

Figure 8:
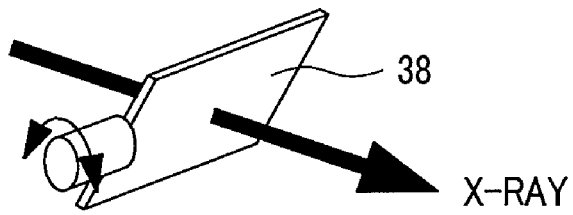
FIG. 8 is a perspective view showing an example of a phase shifter that can be substituted for a wedge for use in measurement to be performed according to a fringe scanning method.

Incidentally, in the measurement based on the fringe scanning method, a phase shifter like the one shown in FIG. 8 can be substituted for the wedge. In this case, the phase shifter 38 is positioned in place of the wedge 26, and rotated in order to change the phase of X-rays. Thus, many interference patterns derived from different phase are formed.

The foregoing processing is performed by the processing unit 30 similarly to the processing to be performed using the Fourier transform method. An image in which a phase difference Δp' caused by the sample is shown as a contrast is displayed on the display unit 31. Moreover, even a background distribution can be eliminated by employing the same measuring procedure as the one to be followed when the Fourier transform method is employed. Incidentally, a phase shift to be varied may be varied by an unequal or equal value each time. Moreover, the wedge 26 or phase shifter 38 is controlled by the control unit 29.

For simulation of the measurement employed in the first embodiment, a virtual sample having a shape shown in FIG. 9A is conceived. FIG. 9B and FIG. 9C show the results of measurement (sample images) achieved by performing numerical calculation. The results of measurement show that when only the sample is positioned as it is conventionally, some shapes of the sample bring about a large phase difference, an interference pattern disappears, and a sample image cannot be produced because of abnormal termination of unwrapping (FIG. 9B).

On the other hand, when an analogous reference object is positioned on the other optical path according to the present invention, a highly visible interference pattern can be formed, and the sample can be accurately observed (FIG. 9C).

According to the first embodiment, a projection image in which a change in the phase of an interference beam caused by a sample is shown as a contrast can be produced. Even when the sample includes a region exhibiting a large density change, such as, bones or lungs and a region exhibiting a small density change, such as, biological soft tissues, the sample can be observed highly sensitively.

Second Embodiment

In the first embodiment, only transmitted image of a sample (a transmissive image) can be obtained. The second embodiment makes it possible to non-destructively observe the inside of a sample. FIG. 10 shows the configuration of an X-ray imaging apparatus in accordance with the second embodiment of the present invention. A sample holder rotating mechanism 39 and a reference object rotating mechanism 40 are added to the components of the first embodiment. A sample is fixed by the sample holder 22, and rotated in (x and z) directions perpendicular to an optical axis by the sample holder rotating mechanism 39. Likewise, the reference object 24 can be rotated in the (x and z) directions perpendicular to the optical axis by the reference object rotating mechanism 40 synchronously with the rotation of the sample.

Figure 11:
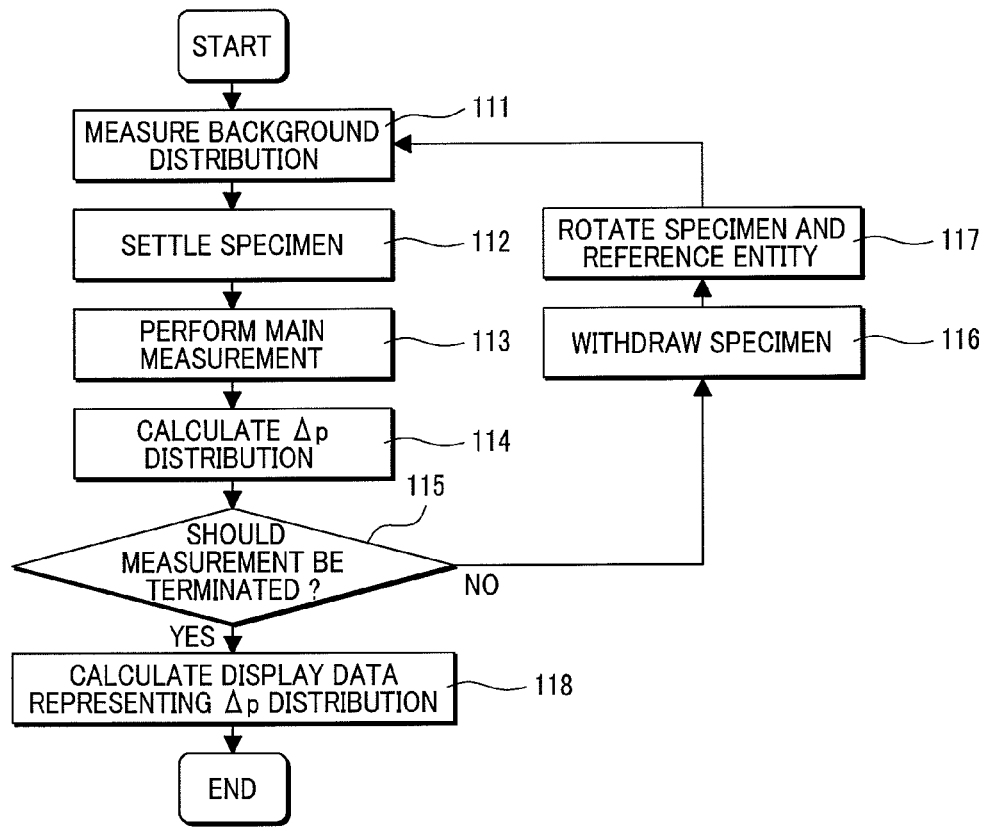
FIG. 11 is a flowchart describing a procedure of eliminating a background distribution from a signal, which represents a phase difference Ap, during measurement employed in the second embodiment.

FIG. 11 is a flowchart describing a procedure for eliminating a background distribution from a signal representing a phase difference Δp during measurement employed in the second embodiment.

At step 111 (measurement of a background), before the sample and reference object are positioned, the Fourier transform method is used to obtain a background distribution (Δpo) of phase values.

At step 112, the sample holder 22 and sample holder positioning mechanism 23 are used to place the sample on an associated optical path, and the reference object positioning mechanism 25 is used to place the reference object 24 on an associated optical path. At this time, the positions of the sample and reference object 24 respectively are adjusted to be nearly identical on the respective beams.

At step 113 (main measurement), the Fourier transform method is used to obtain a distribution ($\Delta p1$) of phase values that is equivalent to a combination of the background distribution and a distribution of phase values affected by the sample.

At step 114, a distribution ($\Delta p1$-$\Delta po$) of values of a phase change caused by the sample and reference object is calculated from the phase distributions obtained at steps 111 and 113 respectively.

At step 115, a decision is made on whether the steps 111 to 114 have been repeated with respect to equiangular positions over a required angle of rotation (=180°/$\Delta r$). If the decision is made in the affirmative (Yes), measurement is completed. If the decision is made in the negative (No) control is passed to step 117.

At step 116, the sample is temporarily withdrawn.

At step 117, the sample rotating mechanism 39 and reference object rotating mechanism 40 are used to rotate the sample and reference object 24 respectively by an angle $\Delta r$. Control is then returned to step 111, measurement is performed with the sample and reference object located at the rotated positions.

At step 118, if the decision is made in the affirmative at step 115, that is, if measurement has been repeated with respect to the equiangular positions over the required angle of rotation (=180°/$\Delta r$), display data representing the distribution $\Delta p$ is calculated.

Data produced after the completion of the measurement is used to subtract a phase shift caused by the reference object from the phase change distribution. A tomographic image in which a phase change $\Delta p$ caused by the sample is shown as a contrast is reconstructed by the processing unit 30, and then displayed on the display unit 31. For calculation for image reconstruction, an algorithm employed in general X-ray CT can be adopted. Moreover, the foregoing measurement procedure is controlled by the control unit 29.

According to the second embodiment, a tomographic image in which a change in the phase of an interference beam caused by a sample is shown as a contrast can be produced non-destructively. Even when the sample includes a region exhibiting a large density change, such as, bones or lungs and a region exhibiting a small density change, such as, biological soft tissues, the sample can be highly sensitively observed.

Third Embodiment

The X-ray interferometer 20 employed in the first and second embodiments is constructed with an monolithic crystal block. Therefore, the size of the interferometer is limited by the diameter of a crystal ingot that is used as a base material. This poses a problem in that an observational field of view of 2 cm or more wide cannot be offered. Described below is an example of an imaging apparatus in which the observational field of view of 2 cm or more wide can be offered by adopting a separated-type X-ray interferometer having the crystal block of the X-ray interferometer separated into two portions.

Figure 12:
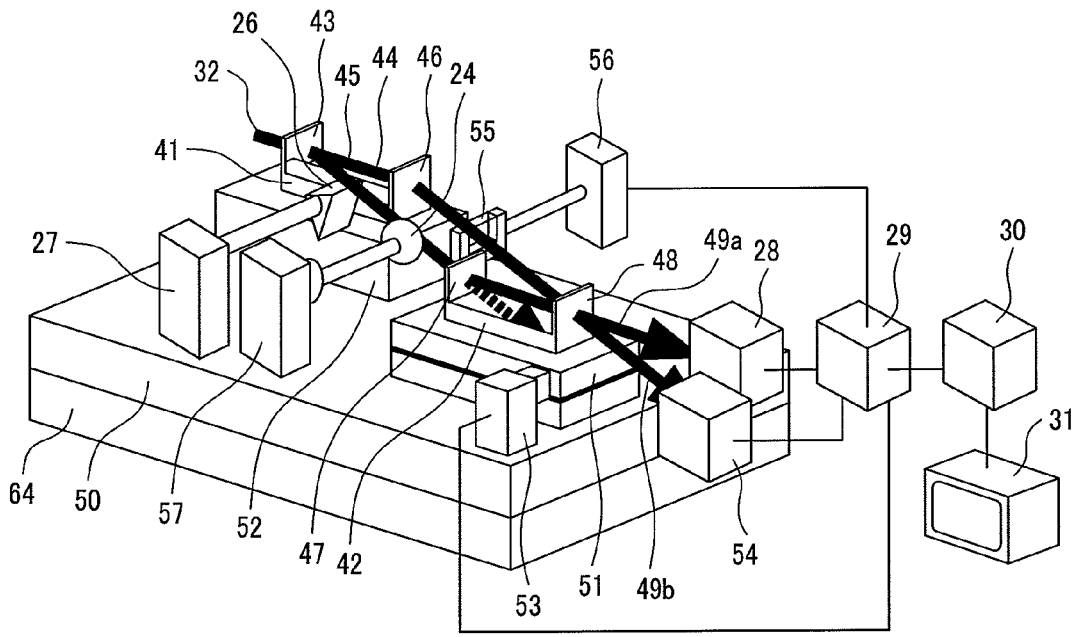
FIG. 12 shows the configuration of an X-ray imaging apparatus in accordance with the third embodiment of the present invention.

FIG. 12 shows the configuration of an X-ray imaging apparatus in accordance with the third embodiment of the present invention. In the third embodiment, a separated-type X-ray interferometer including a first crystal block 41 and a second crystal block 42, each of which has two wafers, is adopted in efforts to expand an observational field of view. Incident X-rays 32 are split into a first beam 44 and a second beam 45 by the first wafer 43 included in the first crystal block 41 due to Laue-case X-ray diffraction. The first beam 44 is diffracted by the second wafer 46 included in the first crystal block 41, and the second beam 45 is diffracted by the third wafer 47 included in the second crystal block 42. The first and second beams are routed to the same point on the fourth wafer 48 included in the second crystal block 42, and are then recombined. Consequently, a first interference beam 49a and a second interference beam 49b are formed.

In the separated-type X-ray interferometer, a relative rotational movement made about a Z axis by the separated crystal blocks (41 and 42) is manifested as a variation in a phase difference between interfering beams. Consequently, the rotational movement has to be highly precisely controlled in order to achieve stable imaging. The relationship between the rotational movement $\Delta \theta$ and the variation $\Delta \phi$ in the phase of an interference beam is given is by the equation (14) presented below.

$$\Delta\phi = 2\pi\Delta\theta(x+t)/d \qquad (14)$$

where t denotes the thickness of the fourth wafer 48, x denotes the space between the third wafer 47 and fourth 20 wafer 48, d denotes the lattice spacing of Laue diffraction, and $\theta_B$ denotes a Bragg angle. According to the equation (14), assuming that Si (220) crystal (d=0.192 nm) diffraction is used, when conditions are such that a wavelength $\lambda$ is 0.07 nm, the thickness t is 1 mm, the space x is 63 mm, and the Bragg angle $\theta_B$ is 10.5°, the rotational movement $\Delta\theta$ relevant to the variation $\Delta\phi$ of $2\pi$ is approximately 2 nano radian. Consequently, for stable measurement, the rotational movement $\Delta\theta$ should be controlled with the positioning precision of at least a sub-nano radian.

In order to attain the above positioning precision, according to the third embodiment, the crystal blocks are positioned by a set of stages (a first $\theta$ table 50 responsible for rotation about a $\theta$ axis of an entire interferometer, a second $\theta$ table 51 that rotates the second crystal block 42 about the $\theta$ axis, and a tilt table 52 that rotates the first crystal block 41 about a $\phi$ axis) whose mechanical rigidity are improved by using a solid bearing mechanism that is made of a slippery material exhibiting nearly identical coefficients of dynamical friction and statical friction. A high-precision positioning mechanism 53 that employs a piezoelectric element or the like is used for the second $\theta$ table 51 that is requested to be positioned with the precision of a sub-nano radian. Moreover, the set of stages is positioned on a vibration isolated table 64 in order to minimize the adverse effect of floor vibration or the like. Furthermore, a control mechanism for controlling the rotations of the crystal blocks using a feedback loop is newly added to the control unit 29 in order to suppress a drift in the long-term rotational movement $\Delta\theta$.

The control mechanism is realized with a mechanism that controls the rotation of the second $\theta$ table 51 via the positioning mechanism 53 so as to cancel a variation in the intensity of the interference beam 49a, which is detected by the detector 54, caused by a drift in the rotational movement $\Delta\theta$. Moreover, if the drift in the rotational movement $\Delta\theta$ cannot be fully suppressed by merely detecting the intensity of the interference beam due to a variation in the intensity of incident X-rays, a two-dimensional detector can be adopted as the detector 54. Moreover, an X-ray interference pattern itself is detected, and the control mechanism is realized with a mechanism that controls the rotation of the second $\theta$ table 51 so as to cancel a drift movement of moiré fringes appearing in the interference pattern.

The sample holder 55, sample holder positioning mechanism 56, and reference object positioning mechanism 57 have the same structures as those included in the first embodiment, and also have the same capabilities as the sample holder rotating mechanism 39 and reference object rotating mechanism 40 included in the second embodiment. Consequently, the inside of a sample can be observed non-destructively by performing the same measurement as that employed in the second embodiment. Moreover, as the reference object 24, the same object as that employed in the first embodiment is adopted.

Measurement is performed in the same manner as it is performed in the first and second embodiments. Based on acquired data, an image in which a change in a phase Δp is shown as a contrast is displayed on the display unit 31.

According to the third embodiment, a projection image or a tomographic image in which a change in the phase of an interference beam caused by even a large sample whose size exceeds 2 cm is shown as a contrast can be non-destructively produced. Even a sample that includes a region exhibiting a large density change, such as, bones or lungs and a region exhibiting a small density change, such as, biological soft tissues can be highly sensitively observed.

Fourth Embodiment

As an example of diagnostic systems that take advantage of the imaging method in accordance with the present invention that the imaging method is highly sensitive to light elements and suitable for observation of biological soft tissues made mainly of the light element, a mammography system is proposed.

Figure 13A:
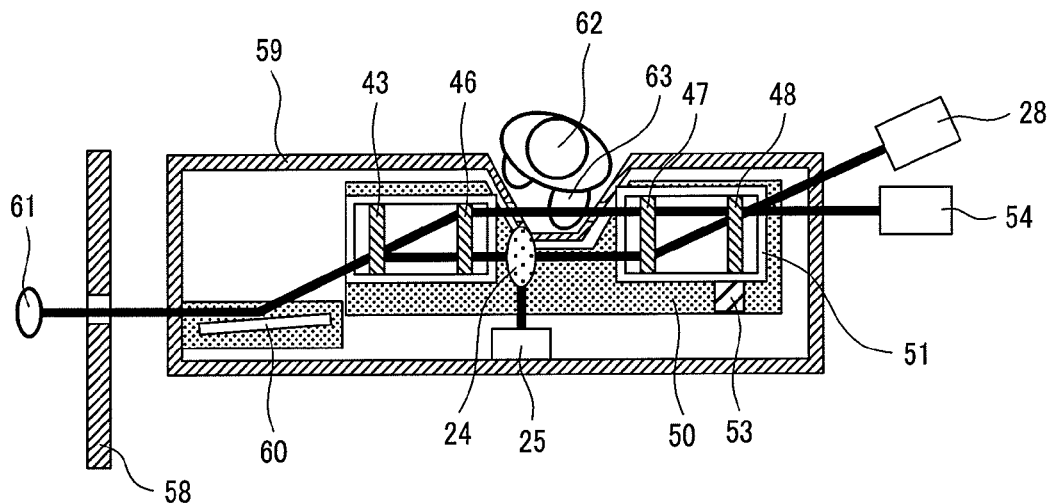
FIG. 13A and FIG. 13B are a plan view and a side view of the configuration of an X-ray imaging apparatus in accordance with the fourth embodiment of the present invention.
Figure 13B:
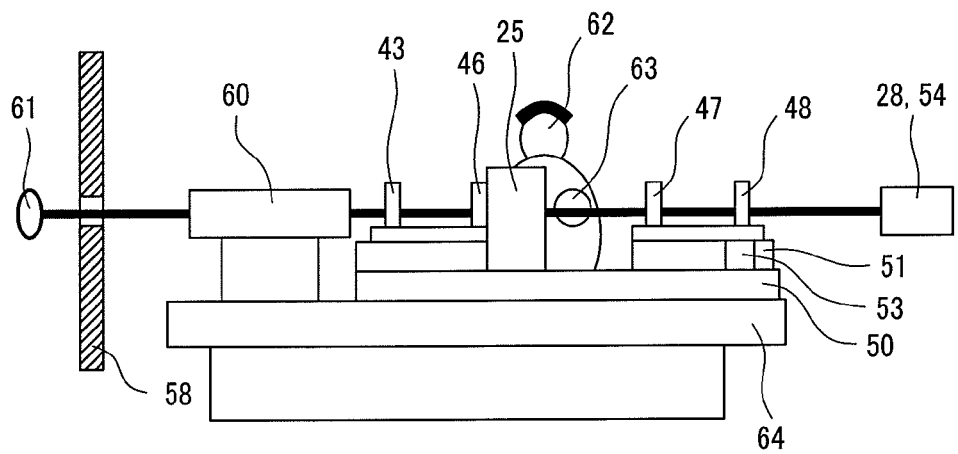

FIG. 13A and FIG. 13B are a plan view and a side view respectively showing the configuration of an X-ray imaging apparatus in accordance with the fourth embodiment of the present invention. For brevity's sake, major components alone are shown. Diagnostic systems are requested to include a means for minimizing an exposure caused by X-irradiation as much as possible, to offer a wide observational field of view within which a subject can be viewed at one time, and to guarantee high stability in producing an unvarying image as a result of every measurement. The fourth embodiment includes, in addition to the basic components of the first and third embodiments, means for preventing X-irradiation to any region of a subject other than an irradiation region, such as, an X-ray protection wall 58 and an X-ray protection cover 59, and a magnification asymmetric crystal plate 60 that magnifies an X-ray beam.

The X-ray protection wall 58 is interposed between an X-ray source 61 and the magnification asymmetric crystal plate 60, blocks unnecessary X-rays out of X-rays irradiated from the X-ray source 61, and is realized with a thick wall whose material contains lead or the like. The X-ray protection wall 58 can block nearly 100% in terms of the intensity of X-rays. The X-ray protection cover 59 covers the magnification asymmetric crystal plate 60 as well as an X-ray interferometer and other major components of the X-ray imaging apparatus. The X-ray protection cover 59 prevents scattering X-rays, which are caused by the wafers (43, 46, 47, and 48) included in the X-ray interferometer, from falling on a subject 62, the X-ray image detector 28, and the detector 54 alike. Since the intensity of the scattering X-rays is not so strong, an acrylic plate containing lead or an iron plate to which a thin lead sheet is bonded can be adopted as the X-ray protection cover. The X-ray protection cover is, as shown in FIG. 13, shaped to be concave in a place where the subject 63 is exposed to an X-ray beam. X-rays will not be irradiated to any region of the subject 63 other than a region thereof to which X-rays should be irradiated.

Distortions or the like of the second wafer 46 included in the first crystal block 41 and the third wafer 47 included in the second crystal block 42 respectively which are caused by heat emitted from the subject 62 can be suppressed by separating the subject 62 from the wafers by a distance of 30 cm or more. Moreover, an adverse effect of floor vibration occurring when the subject 62 is coming or leaving can be suppressed by adopting vibration isolating table 64 carrying the magnification asymmetric crystal plate 60 and X-ray interferometer. The vibration isolating table 64 is also shaped to be concave near the place where the subject lies down, and is structured for fear the subject may come into contact with the vibration isolating table. In efforts to realize measurement ensuring high reproducibility, the second θ table 51 is positioned through feedback control that resembles the one employed in the third embodiment.

Figure 14:
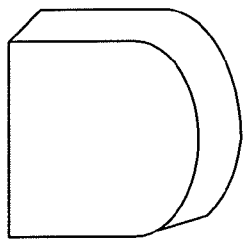
FIG. 14 shows an example of a reference object.

As the reference object 24, a gel-type organic member which is shaped like an object 63 by measuring the subject 63 in advance without use of X-rays (the density is nearly the same as the density of a biological soft tissue that is the object) should be adopted. Otherwise, when the object 63 is stretched thinly using flat plates in the same manner as it is during measurement performed by a mammography system, a D-shaped organic member having the same thickness as shown in FIG. 14 may be adopted.

Using the apparatus, the measurement is, as described in relation to the first embodiment, performed according to the procedure described in the flowchart of FIG. 7. An image in which a phase shift caused by the object 63 is shown as a contrast is calculated by the processing unit 30, and the results of the calculation are displayed on the display unit 31.

What is claimed is:

1. An X-ray imaging apparatus, comprising:
   an X-ray interferometer including a splitting device that splits an incident X-ray beam into first and second X-ray beams, a reflecting device that reflects the first and second X-ray beams, and a combining device that combines the reflected first and second X-ray beams;
   a means for positioning a sample on the path of one of the first or second X-ray beams;
   a means for positioning a reference object, of which shape and internal density distribution are analogous to those of the sample and which is known, on the path of the other X-ray beam different from the X-ray beam in which the sample is positioned;
   a detector that detects an interference X-ray beam emitted from X-ray interferometer; and
   a processing unit that produces a sample image, which shows a phase shift in the interference X-ray beam caused by the sample, on the basis of an output of the detector.

2. The X-ray imaging apparatus according to claim 1, further comprising a means for positioning a phase shifter on the path of one of the first or second X-ray beams.

3. The X-ray imaging apparatus according to claim 2, wherein the X-ray interferometer is formed by a single crystal block having a plurality of crystal wafers and a base, which bears the plates, integrated thereinto.

4. The X-ray imaging apparatus according to claim 2, wherein the X-ray interferometer is formed with a combination of a plurality of single crystal blocks each having a plurality of crystal wafers and a base, which bears the plates, integrated thereinto.

5. The X-ray imaging apparatus according to claim 2, wherein the shape of the phase shifter is like a wedge.

6. The X-ray imaging apparatus according to claim 1, further comprising:
- a first rotating means allowing the means, which places the sample on the path of one of the first or second X-ray beams, to rotate the sample on the path of the X-ray beam; and
- a second rotating means allowing the means, which places the reference object, of which shape and internal density distribution are analogous to those of the sample and which is known, on the path of the other X-ray beam different from the X-ray beam in which the sample is positioned, to rotate the reference object on the path of the other X-ray beam, wherein:
- the first and second rotating means enable simultaneous rotations of the sample and reference object respectively in units of the same angle of rotation; and
- the processing unit includes a means for reproducing a tomographic image of the sample using a plurality of sample images produced by rotating the sample and reference object alike.

7. The X-ray imaging apparatus according to claim 1, wherein the X-ray interferometer is formed by a single crystal block having a plurality of crystal wafers and a base, which bears the plates, integrated thereinto.

8. The X-ray imaging apparatus according to claim 1, wherein the X-ray interferometer is formed by a combination of a plurality of single crystal blocks each having a plurality of crystal wafers and a base, which bears the plates, integrated thereinto.

9. The X-ray imaging apparatus according to claim 1, wherein the reference object whose shape and internal density distribution are analogous to those of the sample and which is known is formed by firming the skeleton of an individual, which belongs to the same species as a small animal adopted as the sample, using an organic material so that the appearance thereof will resemble that of the small animal.

10. An X-ray imaging apparatus, comprising:
- an X-ray interferometer including an X-ray source, a means for reshaping and magnifying a beam emitted from the X-ray source, and a means for splitting the reshaped and magnified beam into first and second X-ray beams, reflecting the beams, and combining the beams;
- a means for positioning a sample on the path of one of the first or second X-ray beams;
- a means for positioning a reference object, of which shape and internal density distribution are analogous to those of the sample and which is known, in the other one of the first and second X-ray beams different from the beam in which the sample is positioned;
- a means for positioning a phase shifter on the path of one of the first or second X-ray beams;
- a means for preventing X-irradiation to any region other than a beam irradiation region of the sample;
- a detector that detects an interference X-ray beam emitted from the X-ray interferometer; and
- a processing unit that produces a sample image, which shows a phase shift in the interference X-ray beam caused by the sample, on the basis of an output of the detector.

11. The X-ray imaging apparatus according to claim 9, wherein the X-ray interferometer is formed with a combination of a plurality of single crystal blocks each having a plurality of crystal wafers and a base, which bears the plates, integrated thereinto.

12. The X-ray imaging apparatus according to claim 10, further comprising a positioning mechanism that adjusts the angles of rotation by the respective crystal blocks are rotated, wherein the positioning precision is 1 nano radian or less.

13. The X-ray imaging apparatus according to claim 10, wherein the shape of the phase shifter is like a wedge.

14. The X-ray imaging apparatus according to claim 9, wherein the reference object whose shape and internal density distribution are analogous to those of the sample and which is known is formed by firming the skeleton of an individual, which belongs to the same species as a small animal adopted as the sample, using an organic material so that the appearance thereof will resemble that of the small animal.

15. An X-ray imaging method, comprising the steps of:
- splitting an incident X-ray beam into mutually interfering first and second beams;
- positioning a sample and a reference object, of which shape and internal density distribution are analogous to those of the sample and which is known, on the paths of the first and second beams respectively;
- combining the fist and second beams that are transmitted the sample and reference object respectively; and
- producing an image, in which a phase shift caused by the sample is shown, on the basis of an interference beam produced by combining the beams.

16. The X-ray imaging method according to claim 15, wherein the phase shift caused by the sample is calculated based on a plurality of sample images produced using different values of a phase difference between the first and second beams which is derived from movement of a phase shifter positioned in the first or second beam.

17. The X-ray imaging method according to claim 16, wherein the phase shift caused by the sample is calculated by subtracting a phase shift caused by the reference object from the phase shift in the interference beam.

18. The X-ray imaging method according to claim 16, wherein a tomographic image of the sample is reproduced using a plurality of sample images produced by simultaneously rotating the sample and reference object about the path of an X-ray beam, and irradiating X-rays in a plurality of different directions.

19. The X-ray imaging method according to claim 15, wherein the phase shift caused by the sample is calculated by subtracting a phase shift caused by the reference object from the phase shift in the interference beam.

20. The X-ray imaging method according to claim 15, wherein a tomographic image of the sample is reproduced using a plurality of sample images produced by simultaneously rotating the sample and reference object about the path of an X-ray beam, and irradiating X-rays in a plurality of different directions.

* * * * *